United States Patent
Cheng et al.

(10) Patent No.: US 11,220,661 B2
(45) Date of Patent: Jan. 11, 2022

(54) COMPOSITIONS COMPRISING TAURATE SURFACTANTS AND METHODS OF USING THE COMPOSITIONS

(71) Applicant: Colgate-Palmolive Company, New York, NY (US)

(72) Inventors: Shujiang Cheng, Warren, NJ (US); Junhong Mao, Plainsboro, NJ (US); Zeenat Nabi, Cranbury, NJ (US); Laurence Du-Thumm, Princeton, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 189 days.

(21) Appl. No.: 16/474,125

(22) PCT Filed: Dec. 27, 2016

(86) PCT No.: PCT/US2016/068656
§ 371 (c)(1),
(2) Date: Jun. 27, 2019

(87) PCT Pub. No.: WO2018/125033
PCT Pub. Date: Jul. 5, 2018

(65) Prior Publication Data
US 2020/0148980 A1     May 14, 2020

(51) Int. Cl.
C11D 17/00    (2006.01)
C11D 1/28     (2006.01)
C11D 3/04     (2006.01)
C11D 3/12     (2006.01)
C11D 3/20     (2006.01)

(52) U.S. Cl.
CPC .............. *C11D 17/006* (2013.01); *C11D 1/28* (2013.01); *C11D 3/046* (2013.01); *C11D 3/1213* (2013.01); *C11D 3/2065* (2013.01); *C11D 3/2075* (2013.01)

(58) Field of Classification Search
CPC ....... C11D 17/006; C11D 1/28; C11D 3/2075; C11D 3/349; A61K 8/0216
See application file for complete search history.

(56) References Cited

U.S. PATENT DOCUMENTS 4,800,197 A * 1/1989 Kowcz ................... A61P 17/00
                                                                    514/162
5,710,141 A * 1/1998 Lin ......................... A61Q 19/08
                                                                    514/162

(Continued)

OTHER PUBLICATIONS

Anonymous, "Sodium methyltaurate isopalmitate," www.thegoodcentscompany.com/data/rw1794181.html, [Retrieved from internet Dec. 6, 2016].

(Continued)

*Primary Examiner* — Necholus Ogden, Jr.

(57) ABSTRACT

A bar soap composition is made from ingredients comprising: at least one cleanser chosen from soap and a first surfactant; and at least one taurate surfactant chosen from a salt of a fatty acid amide of taurine, a salt of a fatty acid amide of N-methyl taurine, and combinations thereof. The taurate surfactant is different than the first surfactant. The composition is in a solid bar form. Other personal care and home care products that include the taurate surfactants are also disclosed.

8 Claims, 4 Drawing Sheets

Cell Migration experiment results (HaCaT Cells) after 24 hours. (% Reduction in Gap Distance)

(56) References Cited

U.S. PATENT DOCUMENTS

| | | | |
|---|---|---|---|
| 6,344,435 B1* | 2/2002 | Miyahara | C07C 309/14 510/494 |
| 8,865,147 B2 | 10/2014 | Rizk et al. | |
| 9,006,162 B1 | 4/2015 | Rizk | |
| 9,856,441 B2 | 1/2018 | Gu | |
| 9,877,905 B2* | 1/2018 | Dixon | A61K 8/466 |
| 2007/0172431 A1* | 7/2007 | Galumbeck | A61K 8/678 424/47 |
| 2009/0062406 A1 | 3/2009 | Loeffler | |
| 2012/0121721 A1* | 5/2012 | James | A61K 8/9789 424/537 |
| 2017/0335251 A1 | 11/2017 | Nabi | |

OTHER PUBLICATIONS

Anonymous, 2016, "Sodium Methyl Cocoyl Taurate," https://www.truthinaging.com/ingredients/sodium-methyl-cocoyl-taurate [Retreived from internet Jun. 26, 2019].
Chemical Book, 2016, "Sodium-N-methyl-N-oleyl taurate," https://www.chemicalbook.com/chemicalproductproperty_en_CB5506350.htm [Retrieved from internet Nov. 14, 2016].
Compagnie Française Des Produits Thermaux, 2002, "Vitalite Soap," Mintel Database GNPD AN:162918.
CosDNA, 2009, "Sodium taurine cocoyl methyltaurate," [Retrieved from internet Jun. 26, 2019] http://www.cosdna.com/eng/fdccf510963.html.
Cosmetic Ingredient Review, 2015, "Safety Assessment of Alkyl Taurate Amides and Taurate Salts as Used in Cosmetics," Final Report https://www.cir-safety.org/sites/default/files/taurat092015Tent.pdf.
CVS Pharmacy, 2006,"Sensitive Skin Beauty Bar Soap," Mintel Database GNPD AN:10254025.
EWG's Skin Deep Cosmetics Database, 2007, "Sodium Methyl Cocoyl Taurate," https://www.ewg.org/skindeep/ingredient/706122/SODIUM_METHYL_COCOYL_TAURATE/ [Retrieved from internet Jun. 26, 2019].
EWG's Skin Deep Cosmetics Database, 2007, "Sodium Methyl Oleyl Taurate," https://www.ewg.org/skindeep/ingredient/706124/SODIUM_METHYL_OLEYL_TAURATE/ [Retrieved from internet Jun. 26, 2019].
EWG's Skin Deep Cosmetics Database, 2007, "Sodium Methyl Stearoyl Taurate," https://www.ewg.org/skindeep/ingredient/706125/SODIUM_METHYL_STEAROYL_TAURATE/ [Retrieved from internet Jun. 26, 2019].
Indústrias Matarazzo De Óleos E Derivados, 2002, "Baby Soap Bar," Mintel Database GNPD AN: 176584.
Innospec, 2005, "inner beauty formulation guide," Retrieved from the Internet: URL:https://www.ulprospector.com/documents/1036650.pdf?bs=3904&b=97777&st=20, pp. 1-28.
Innospec, 2014, "Formulations," Retrieved from the Internet: URL:https://www.ulprospector.com/documents/1273346.pdf?bs=3904&b=376525&st=20 [Retrieved on Feb. 23, 2017], p. 24PP.
Innospec, 2015, "inner beauty product guide," Retrieved from the Internet: URL:https://www.ulprospector.com/documents/1386268.pdf?bs=3904&b=431422&st=20, [Retrieved on Feb. 22, 2017] pp. 1-24.
International Search Report and the Written Opinion of the International Searching Authority issued in International Application PCT/US2016/068656 dated Mar. 10, 2017.
Method Products, 2011,"Moisturising Hand Wash," Mintel Database GNPD AN: 1633904.
Moong Pattana Marketing, 2010, "Baby Soap Refill Pack," Mintel Database GNPD AN: 1366172.
Ren Q, 2016, "Face washing milk useful for diminishing facial inflammation comprises e.g. laoshan mountain green tea extract, lily extract liquid, jojoba seed oil, isopropyl palmitate, coconut oil fatty acid monoethanolamide, gum Arabic and chitosan," Database WPI Week 201679 Thomson Scientific, London, GB; AN 2016-456905.
Sinter Futura, 2006,"Childrens' Soap," Mintel Database GNPD AN: 616268.

* cited by examiner

Cell Migration experiment results (HaCaT Cells) after 24 hours. (% Reduction in Gap Distance)

Multiple Inflammation Biomaker Assay Results (MatTek 3D EpiDerm)
Reported in % control Multiple Inflammation Biomaker Assay Results (MatTek 3D EpiDerm)
Reported in % control Multiple Inflammation Biomaker Assay Results (MatTek 3D EpiDerm)
Reported in % control Multiple Inflammation Biomaker Assay Results (MatTek 3D EpiDerm)
Reported in % control

COMPOSITIONS COMPRISING TAURATE SURFACTANTS AND METHODS OF USING THE COMPOSITIONS

BACKGROUND

Skin can be compromised or irritated as a result of various factors, e.g. harsh climate, low hydration level, and so forth. As such, there is a need for products which do not further irritate or compromise the skin; and that promote skin cell viability and/or skin barrier repair.

Taurine, or 2-aminoethylsulphonic acid, is a non-proteinogenic amino acid that is known to have skin health benefits. For instance, taurine is known to exhibit antioxidant properties, regulate inflammatory reactions and enhance skin barrier repair. Taurine has been incorporated in various forms of personal care products and its skin health benefits have been documented both on lab skin models and clinical evaluations.

However, taurine shows stability issues in some formulations, such as bar soap. In particular, taurine tends to recrystallize on the surface of bar soap after aging. The recrystallized taurine can cause an undesirable look and/or feel to the bar soap product.

Taurine based surfactants, such as sodium methyl oleoyl taurate and sodium methyl cocoyl taurate, are known to be mild and high-foaming surfactants. They have been employed in certain personal care products. However, the taurine moiety of these surfactants is covalently bonded to a fatty acid group that does not dissociate in solution to provide for availability of free taurine. Because the taurine moiety is tied up in solution with the fatty acid group, one of ordinary skill in the art would not expect the taurate surfactants to have the above described skin health benefits associated with taurine.

While compounds such as taurine are known for improving skin health, discovering additional compounds that have skin health benefits and that are otherwise compatible with personal care and home care products would be a welcome advancement in the art.

BRIEF SUMMARY

An embodiment of the present disclosure is directed to a bar soap composition. The composition is made from ingredients comprising: at least one cleanser chosen from soap and a first surfactant; and at least one taurate surfactant chosen from a salt of a fatty acid amide of taurine, a salt of a fatty acid amide of N-methyl taurine, and combinations thereof. The taurate surfactant is different than the first surfactant. The composition is in a solid bar form.

Another embodiment of the present disclosure is directed to a composition made from ingredients comprising at least one taurate surfactant chosen from a salt of a fatty acid amide of taurine, a salt of a fatty acid amide of N-methyl taurine, and combinations thereof. The composition is in the form of a personal care product or home care product. If the composition is a personal care product in the form of a shampoo, the composition 1) does not include more than 0.1% of a mono ester anionic surfactant and does not include more than 0.1% of an amphoteric amide surfactant, 2) does not include more than 0.01 weight % of silicone Quaternium-8, and 3) is either (i) not both a shampoo and a conditioner or (ii) comprises at least one of a sulfate based surfactant or a polydimethylsiloxane.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
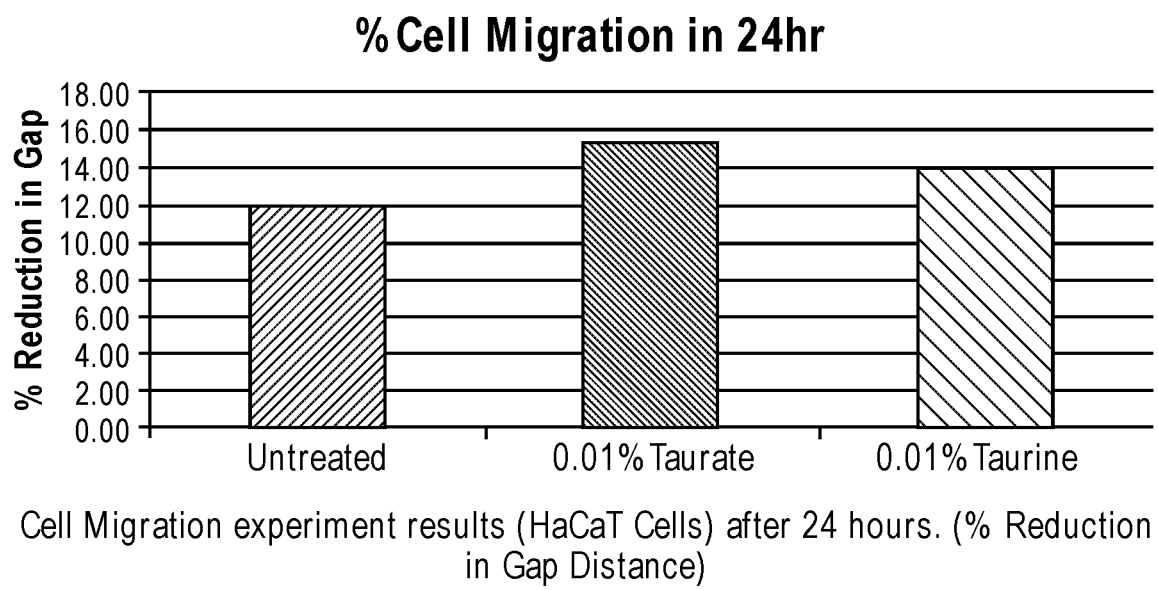
FIG. 1 depicts data collected from Cell Migration experiments using HaCaT Cells and shows a % Reduction in Gap Distance after 24 hours, as described in the Examples below.
Figure 2A:
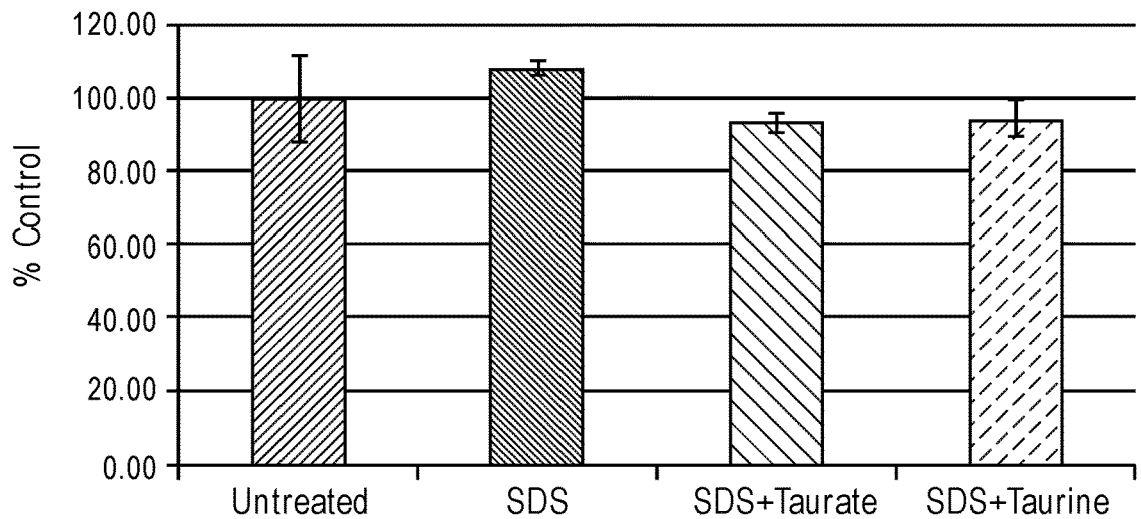
FIGS. 2A-2D represent data collected from Multiple Inflammation Biomaker Assay experiments using MatTek 3D EpiDerm and reported in % control, as described in the Examples below.
Figure 2B:
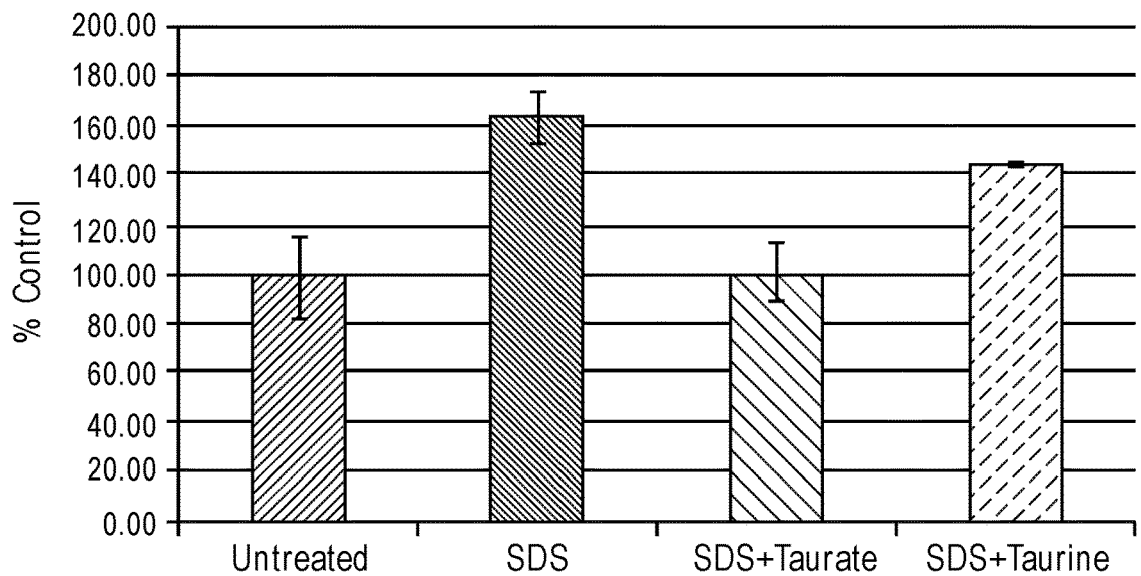
Figure 2C:
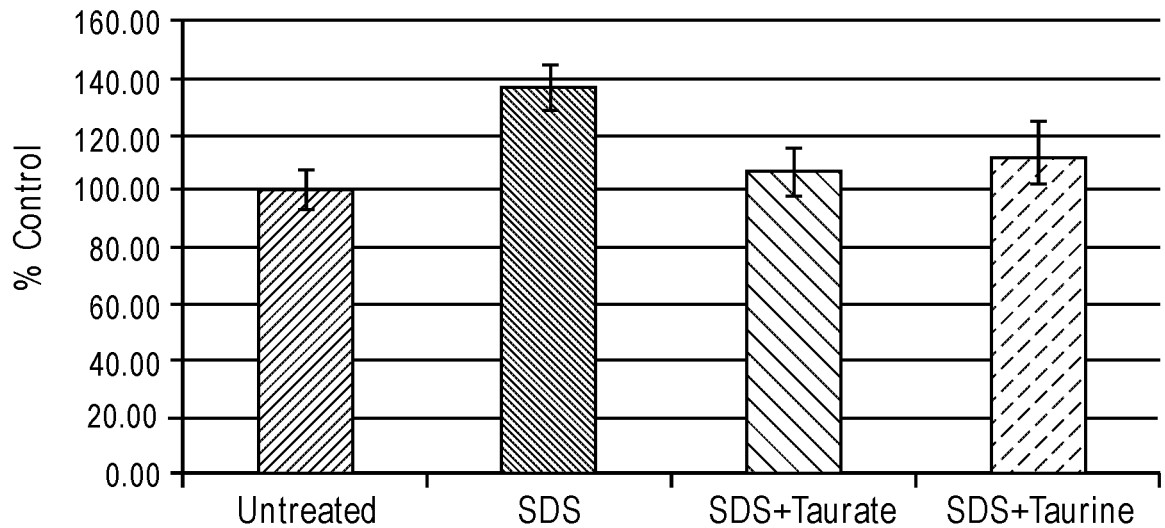
Figure 2D:
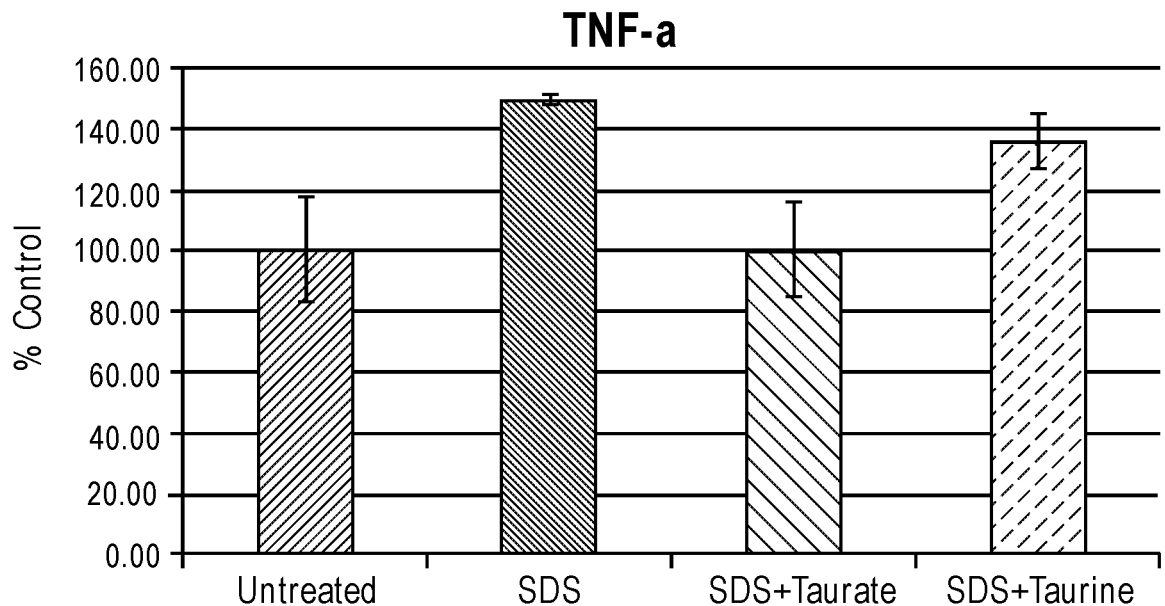

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

An embodiment of the present disclosure is directed to a composition made from an ingredient comprising at least one taurate surfactant chosen from a salt of a fatty acid amide of taurine, a salt of a fatty acid amide of N-methyl taurine, and combinations thereof. The composition is in the form of a personal care or home care product, including, for example, a body wash, a bar soap, a shower gel, a shampoo, a conditioner, a hand soap, a facial wash, a cream, a hand and body lotion, a dish liquid, an insect repellant, a gel, a roll-on, a deodorant, an antiperspirant or a pump spray.

In an embodiment, the fatty acid chains of the taurate surfactants have 6 carbon atoms or more. In an embodiment, the taurate surfactant includes a fatty acid chain having 12 to 25 carbon atoms. The specified number of carbon atoms of the fatty acid chains described herein indicate the average chain length of the fatty acid chain, and lesser amounts of taurate surfactants having chain lengths that are shorter or longer that the lengths that are specified can be included, depending on the degree of purification used for making the particular ingredient, as would be understood by one of ordinary skill in the art. Blends of various lengths of fatty acids can be employed. Specific examples of such taurate surfactants include any of the compounds of general formula 1:

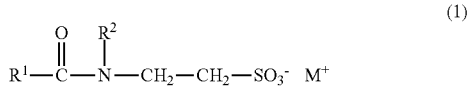

wherein $R^1$ is a saturated or unsaturated, straight or branched alkyl or alkenyl group with 12 to 25 carbon atoms, such as 14 to 20 carbon atoms; $R^2$ is H or methyl and M is sodium, potassium, calcium, magnesium or ammonium. Suitable examples are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, sodium n-isostearoyl methyltaurate, calcium lauroyl taurate, magnesium methyl cocoyl taurate, sodium methyltaurate isopalmitamide and mixtures thereof. Still other examples of taurate surfactants include sodium methyltaurine cocoyl methyltaurate and sodium taurine cocoyl methyltaurate.

In an embodiment, the taurate surfactants are compounds in which $R^2$ is a methyl group and $R^1$ has 16 to 18 carbon atoms; such as, for example, sodium methyl oleyl taurate, sodium methyl cocoyl taurate and combinations thereof. In an embodiment, the taurate surfactant is sodium methyl oleyl taurate.

In an embodiment, if the composition is in the form of a shampoo, the composition 1) does not include more than 0.1% of a mono ester anioinic surfactant and does not include more than 0.1% of an amphoteric amide surfactant, 2) does not include more than 0.01 weight % of silicone Quaternium-8, and 3) is either (i) not both a shampoo and a conditioner or (ii) comprises at least one of a sulfate based surfactant or a polydimethylsiloxane. In an embodiment, the personal care composition also does not include a medically effective amount of salicylic acid. In embodiments, the composition also does not include an olive oil-based compound and/or a quaternary ammonium salt. The phrase "olive oil-based compound" is defined herein to include olive oil and derivatives of olive oil that provide skin moisturizing benefits that are similar to those benefits associated with olive oil, including olive oil polyethyleneglycol (PEG) esters (including derivatives thereof, such as, but not limited to, olive oil PEG-6 esters, olive oil PEG-7 esters, olive oil PEG-10 esters), olive oil extract, olive husk extract, olive leaf extract, olive oil unsaponifiables, olive oil fatty acid derivatives, olivamidopropyl (and derivatives thereof, such as, but not limited to, olivamidopropyl dimethylamine, olivamidopropyl dimethylamine lactate, and olivamidopropyl betaine), olivamide DEA, and olivamidopropalkonium chloride.

In an embodiment, the compositions of the present disclosure further comprise a carrier comprising a personal care ingredient. The personal care ingredient is selected from, for example, a fragrance, a preservative, a solvent, a propellant, a skin cell renewal agent, an anti-acne drug, an antiperspirant compound, an insect repellent agent, a sunscreen agent, a decomposition product of an oil or a fat, an exfoliant, a surfactant, a soap and a mixture of two or more thereof.

The compositions of the present disclosure can have benefits similar to those of taurine when included in compositions that come in contact with the skin. These benefits can include at least one of reducing skin irritation and/or improving a cellular repair function of the skin.

Another embodiment of the present disclosure is directed to a bar soap composition made from ingredients comprising: at least one cleanser chosen from soap and a first surfactant (sometimes referred to herein as a cleanser surfactant); and at least one taurate surfactant chosen from a salt of a fatty acid amide of taurine, a salt of a fatty acid amide of N-methyl taurine, and combinations thereof, the taurate surfactant being different than the first surfactant. The composition is in a solid bar form.

In an embodiment, the at least one cleanser employed in the bar soap is a soap. The term "soap" is defined herein as a salt of a fatty acid. In an embodiment, the soap is a salt of a $C_8$-$C_{22}$ carboxylic acid. For example, the salt can comprise at least one compound chosen from an alkali metal, such as sodium, or alkylammonium salt of a $C_8$-$C_{22}$ carboxylic acid, such as about a $C_{12}$-$C_{18}$ carboxylic acid. The amount of soap can range from about 60 weight % to about 95 weight %, such as about 70 weight % to about 80 weight %, based on the total weight of the final bar soap composition.

The fatty acid soap may comprise a neutralized fatty acid. Typical fatty acids used for soaps include myristic acid, lauric acid, palmitic acid, and stearic acids, as examples. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils.

The fatty acids may be neutralized with any base to form a soap. Typical bases include, but are not limited to, sodium hydroxide, potassium hydroxide, and triethanolamine. In certain embodiments, the fatty acid soap is formed from fatty acids neutralized by two or more bases. For example, sodium soaps, ammonium soaps, potassium soaps, magnesium soaps and calcium soaps can each be used alone as the soap ingredient, or as mixtures of two or more of the sodium, ammonium, potassium, magnesium and calcium soaps.

The soap can be made either in situ in amalgamate by mixing a source of fatty acids with the neutralizing agent, or the soap may be provided in a pre-made form. In certain embodiments, the molar amount of fatty acids is greater than the molar amount of neutralizing agent such that fatty add remains in the amalgamate/pre-made soap. In some embodiments, the fatty acid soap is provided in the composition in the form of soap chips, as is known in the art.

The cleanser surfactant can be any surfactant suitable for use in bar soap. Examples of suitable surfactants can include PEG-12 and other PEGs, Polysorbate 20 and other polysorbates, synthetic detergents (e.g., Sodium Lauroyl Isethionate, sodium isethionate, etc.), Sodium tailowate, Cocamidopropyl betaine and Sodium salts of vegetable oils.

Any of the taurate surfactants disclosed herein, or combinations thereof, can be employed in the bar soap compositions of the present disclosure. The taurate surfactants can be in any suitable concentrations so long as the taurate surfactants remain stable in the bar soap formulation. Examples of suitable taurate surfactant concentrations range from about 0.1% to about 10% by weight of the final bar soap composition, such as about 0.1% to about 5% by weight of the composition, or about 1% to about 3% by weight of the composition. In an embodiment, the taurate surfactant, such as those of formula 1, are the only surfactants employed in the compositions of the present disclosure (e.g., where soap, rather than the first surfactant, is used as the cleanser), thereby providing one or more of the benefits described herein while potentially also acting as a surfactant.

Other ingredients can also be added to the bar soap. Examples of such ingredients include structuring agents, skin conditioning agents, chelating agents, foam boosters, preservatives, antimicrobial agents, exfoliating/scrubbing particles, glycerine, sodium chloride, titanium dioxide, colorants, fragrances and water. In an embodiment, the bar soap comprises at least one of glycerine and sodium chloride.

Suitable structuring agents (which may sometimes be referred to herein as structurants) include, for example, gellants selected from the group consisting of dibenzylidene sorbitol, dibenzylidene xylitol, dibenzylidene ribitol, and mixtures thereof. Other examples of structurants include alkali halides and alkali metal sulfates such as sodium chloride and sodium sulfate. Structurants may be incorporated into the compositions in an amount of up to 2 weight %, such as 0.1 to 1.5 weight % or 0.2 to 1 weight %, relative to the total weight of the final bar soap composition.

Skin conditioning ingredients (including emollients) that may be included in the bar soap compositions include: various fats and oils (for example, soybean oil, sunflower oil, canola oil, and shea butter; glyceryl esters (for example, PEG 6 caprylie/caprie triglycerides, PEG 80 glyceryl cocoate, PEG 40 glyceryl cocoate, PEG 35 soy glyceride); alkyloxylated derivatives of dimethicone (for example, such as PEG/PPG-22/24 Dimethicone and PEG-8 Dimethicone); silicone esters (for example, Dimethicone PEG-7 isostearate); silicone quaternium compounds (for example, Silicone Quaternium-8); lanolin quaternium compounds (For example, quaternium-33); cationic polymers (for example, Polyquaternium-6 and Polyquaternium-7); and silicone polymers (for example, dimethiconol, dimethicone copolyol, alkyl dimethicone copolyol, and dimethicone copolyol amine.

Examples of foam boosters that may be incorporated into the bar soaps include certain amphoteric surfactants, cocomonoethanolamide (CMEA), cocoamidopropylamine oxide, cetyl dimethylamine chloride, decylamine oxide, lauryl/myristyl amidopropyl amine oxide, lauramine oxide, alkyldimethyl amine n-oxide, and myristamine oxide, in certain embodiments, the amount of foam booster is 2 weight % to 10 wt. % of the final bar soap composition.

A chelating agent may also be added to the to help retard oxidation. Any suitable chelating agent can be employed. For example, Ethylenediaminetetraacetic acid (EDTA) and salts thereof can be used as the chelating agent. The chelating agent is preferably present in amounts of about 0.01 wt. % to about 0.2 weight %, or about 0.025 weight % to about 0.1 weight % by total weight of the final bar soap composition, on an active basis.

The compositions of the present disclosure may also contain a preservative and/or antimicrobial agent in an amount of up to 1 weight %, or from about 0.01 wt. % to about 0.5 weight %, of the final bar soap composition on an active basis. Examples of preservatives include, but are not limited to, sorbic acid, potassium sorbate, methyl paraben, propyl paraben, imidazolinylurea, methylchloroisothiazolinone, and hydantoins (for example, DMDM hydantoin). Antimicrobial agents include, for example, triclocarban, triclosan and the like.

Particulate matter that aids exfoliation may further be incorporated into the bar soap. Particular matter includes polyethylene beads, jojoba beads, lufa, and oat flour.

Fragrance can be incorporated into the bar soap compositions in an amount of about 0.001 to about 2 wt. % of the final bar soap composition. The fragrance can include any active agent such as a phenolic, aldehyde, alcohol, nitrile, ether, ketone or ester and the like.

Water may be present in the bar soap in an amount of up to about 20 weight %, up to 15 weight %, or up to 10 weight % by total weight of the final bar soap composition. Preferably, water is present in an amount of from 5 weight % to 20 weight %, or from 8 weight % to 20 weight % or from 8 to 15 weight % of the final bar soap composition. The water can be added separately or made available from water contained in the other ingredients.

The pH of the bar soap composition can range, for example, from about 8.5 to about 12, such as about 9 to about 11, or about 9 to about 10. The pH test method is based on 1 g of bar soap dissolved into 99 g of water to make a 1 weight % soap solution, which is then tested for pH level.

In an embodiment, the final bar soap composition does not include a medically effective amount of antimicrobial agents, such as triclocarban or salicylic acid, for topical applications. The term "not a medically effective amount" as used herein is defined to mean less than 0.01% by weight. In an embodiment, the final bar soap composition includes less than 0.001% or less than 0.00001% of antimicrobial agents, such as triclocarban or salicylic acid, by weight, relative to the total weight of the final bar soap composition.

When added to bar soap formulations, the taurate surfactants, as described herein, can have one or more of the following advantages: reducing skin irritation compared to the same composition made without the taurate surfactant, improving a cellular repair function of the skin compared to the same composition made without the taurate surfactant, or avoiding the problem of recrystallization of taurine in the bar soap, as described above. Thus, employing the taurate surfactants of the present disclosure in bar soap may provide one or more of the same skin health benefits provided by taurine, while avoiding the known recrystallization problems associated with taurine.

As described above, any of the compositions of the present disclosure can be used to alleviate skin irritation, skin inflammation and/or to improve the cellular repair function of the skin. Thus, an embodiment of the present disclosure is directed to a method of reducing skin irritation and/or inflammation. Another embodiment of the present disclosure is directed to a method of improving the cellular repair function of the skin. Both of these methods comprise applying an effective amount of any of the compositions described herein to the skin of a subject.

EXAMPLES

The following in vitro studies evaluate the skin health benefits of sodium methyl oleoyl taurate in comparison with taurine at the same weight concentration. Comparable effects on anti-irritation/anti-inflammation and cellular repair were observed. Results suggest that this new discovery may allow the formulation of sodium methyl oleoyl taurate in bar soaps to achieve the skin health benefits of taurine and avoid taurine stability issues, such as recrystallization.

The materials used in the examples below were as follows:
  HaCat Cell Line (AddexBio, San Diego, Calif.)
  3D EpiDerm skin models (SIT 200 skin irritation model, MatTek Corporation, Ashland, Mass. 01721).
  Taurine (Sigma Aldrich>99% Lot 1419568V)
  Sodium Methyl Oleoyl Taurate (M35676, Rhodia Solvay Group)
  SDS—Sodium Dodecyl Sulfate (MatTek Corporation, Cambridge, Mass.)
  DMEM—Dulbecco's Modified Eagle Medium (Gibco by Life Technologies, Grand Island, N.Y.)

HCYTOMAG-60K-07 Human Cytokine Magnetic Kit (Millipore, Billerica, Mass.)

Example 1—Cell Migration Assay

Three different culture medium samples were prepared. A control medium that included a Dulbecco's modified Eagle's medium (DMEM) comprising actives of 10% Fetal Bovine Serum and 1% Penicillin Streptomycin; a taurine medium that was the same as the control medium but included 0.01% by weight Taurine; and a taurate medium that was the same as the control medium but included 0.01% by weight Sodium Methyl Oleoyl Taurate.

To determine the effect of both Taurine (0.01%) and Sodium Methyl Oleoyl Taurate (0.01%) on the cellular repair function, in vitro experiments were conducted using HaCaT cells. HaCaT cells are a spontaneously transformed aneuploid immortal keratinocyte cell line from adult human skin. Three sample wells of the HaCaT cells were each grown until 100% confluent. After that, each well was scratched with a 1000 microliter (ul) tip (to create the gap) and washed twice with 1 milliliter (ml) of phosphate buffered saline ("PBS") to eliminate dead floating cells. Following that, each one of the three sample wells were treated with 1 ml of one of the three culture medium samples: one with the control medium, one with the taurine (0.01%) medium, and one with the sodium methyl oleoyl taurate (0.01%) medium. Then, initial measurements of gap distance were taken using a microscope (OLYMPUS IX71). Next, the treated cells were incubated for 24 hours and measurements were taken again using the same microscope. The percentage of gap distance reduction is shown in FIG. 1.

The migration assay provided a measure of the cell migration in order to evaluate the active's potential in promoting cell multiplication, and thus inducing barrier repair. The smaller the gap, the greater the migration rate, which suggests better cellular repair function (e.g., improved skin barrier repair). As shown in FIG. 1, the cells treated for 24 hours with the same weight concentration of sodium methyl oleoyl taurate and taurine showed comparable enhancement in cell migration rate.

Example 2—Multiple Inflammation Biomarker Assay

To document the effect on skin inflammation, in vitro experiments using 3D EpiDerm skin models (SIT 200 skin irritation model, MatTek Corporation, Ashland, Mass.) were conducted. An irritant chemical, sodium dodecyl sulfate (0.02 wt. % SDS), was used to induce skin irritation in in vitro skin samples. After the inducement of skin irritation, the in vitro skin samples were each treated topically with one of two 30 ul test solutions (either a 1% Taurine in PBS solution or a 1% Sodium methyl oleoyl taurate in PBS solution) for 1 hour in a tissue culture incubator (37 degree C., 5% $CO_2$). Following the incubation, the skin samples were washed with PBS and placed in a culture medium and further incubated for 24 hours. Tissue was harvested and homogenized for a multiple inflammation biomarker assay, testing levels of IL-1, IL-6, IL-8 and TNF-a. Biomarkers were analyzed by a Milliplex assay kit. (Millipore, Billerica, Mass.).

The irritant chemical, sodium dodecyl sulfate (SDS), that was used is commonly used as a negative control in irritation/inflammation assays on MatTek tissue. The multiple biomarker assay of Example 2 measured the levels of proinflammatory cytokines, including IL-1a, IL-6, IL-8, TNF-a, in one assay to evaluate the level of skin irritation/inflammation. The more cytokines released, the greater the irritation and/or inflammation potential. As shown in FIGS. 2A-2D, SDS induced the expression of cytokines IL-1a, IL-6, IL-8 and TNF-a. However, with the co-treatment of sodium methyl oleoyl taurate or taurine, the cytokine levels were suppressed. It can be concluded that reduced irritation potential is found in tissues treated with sodium methyl oleoyl taurate compared to the samples not treated with either sodium methyl oleoyl taurate or taurine.

Based on the above described cell migration assay and inflammation assay results, sodium methyl oleoyl taurate shows benefits in promoting skin cellular repair (e.g., skin barrier repair) and acting against skin irritation/inflammation that are comparable to those of taurine. The results suggest that sodium methyl oleoyl taurate can potentially be used in bar soap formulations as well as other product forms to deliver the skin benefits that have been previously documented with taurine. And, sodium methyl oleoyl taurate potentially provides improvements over taurine when used in various products (e.g., bar soap and the like) because it is hypothesized that sodium methyl oleoyl taurate may have improved stability in bar soap and thus may not cause the undesirable look and/or feel associated with recrystallized taurine in bar soap formulations.

Example 3—Bar Soap Formulations

Any of the taurate surfactants of the present disclosure can be employed to make a bar soap formulation, as described herein. Example ingredients for such bar soap formulations are shown in Table 1 below.

TABLE 1

| Formulation for bar soap | |
|---|---|
| ≈70% | Sodium soap |
| 8-15% | Water |
| 1-4% | Glycerin |
| 0.2-6% | Taurate Surfactant |
| 0.5-1.3% | Fragrance |
| 0.2-1% | Sodium Chloride |
| 0.1% | Titanium dioxide |
| ≈0-15% | Color |
| pH = 8.5-11 | (1 wt % solution) |

The percentages in Table 1 are weight percentages based on the total weight of the final bar soap composition. All ranges are exemplary only, so that amounts outside of the ranges shown can be employed. The ingredients can be mixed and the bar soap shaped using any suitable method that is known in the art or yet to be developed.

Example 4—Irritation Biomarker (IL-1a) Assay

Two separate combar samples were formulated, one with taurine and one with sodium methyl oleoyl taurate. Both the taurine and sodium methyl oleoyl taurate were formulated at the same molar concentration in the combar samples. The weight concentrations of taurine and methyl oleoyl taurate in their respective combar bases was as follows:

Taurine combar sample—2% Taurine (obtained from Qianjiang Yongan Pharmaceutical, Wuhan, China), 98% Combar;

Taurate combar sample—6.8% Sodium Methyl Oleoyl Taurate (obtained from Rhodia Solvay Group), 93.2% Combar.

Samples for testing were made by mixing the taurine combar and taurate combar in PBS (1% weight by volume combar base of each of the taurine combar and sodium methyl oleoyl taurate combar in PBS).

To document skin inflammation, in vitro experiments were conducted using 3D EpiDerm skin models (SIT 200 skin irritation model, MatTek Corporation, Ashland, Mass.). Separate In vitro skin samples were treated topically with 30 ul each of the taurine combar and taurate combar test samples for 1 hour in a tissue culture incubator. Following the incubation, the skin samples were washed with PBS, placed in a culture medium and allowed to continued to incubate for 24 hours. Tissue was harvested and homogenized for a IL-1a assay. IL-1a levels were analyzed using a Human IL-1 alpha/IL-1F1 Quantikine ELISA kit available from R&D Systems, Minneapolis, Minn. Among cytokines released along the inflammation pathway, IL-1a is recognized as a prominent irritation biomarker. The more IL-1a that is released, the greater is the irritation potential.

Due to high pH and the presence of surfactants in the formulation, it was expected that the combar base would show significantly higher irritation levels compared to untreated skin samples. Thus, the combar base was used as a negative control on the MatTek tissue.

Figure 3:
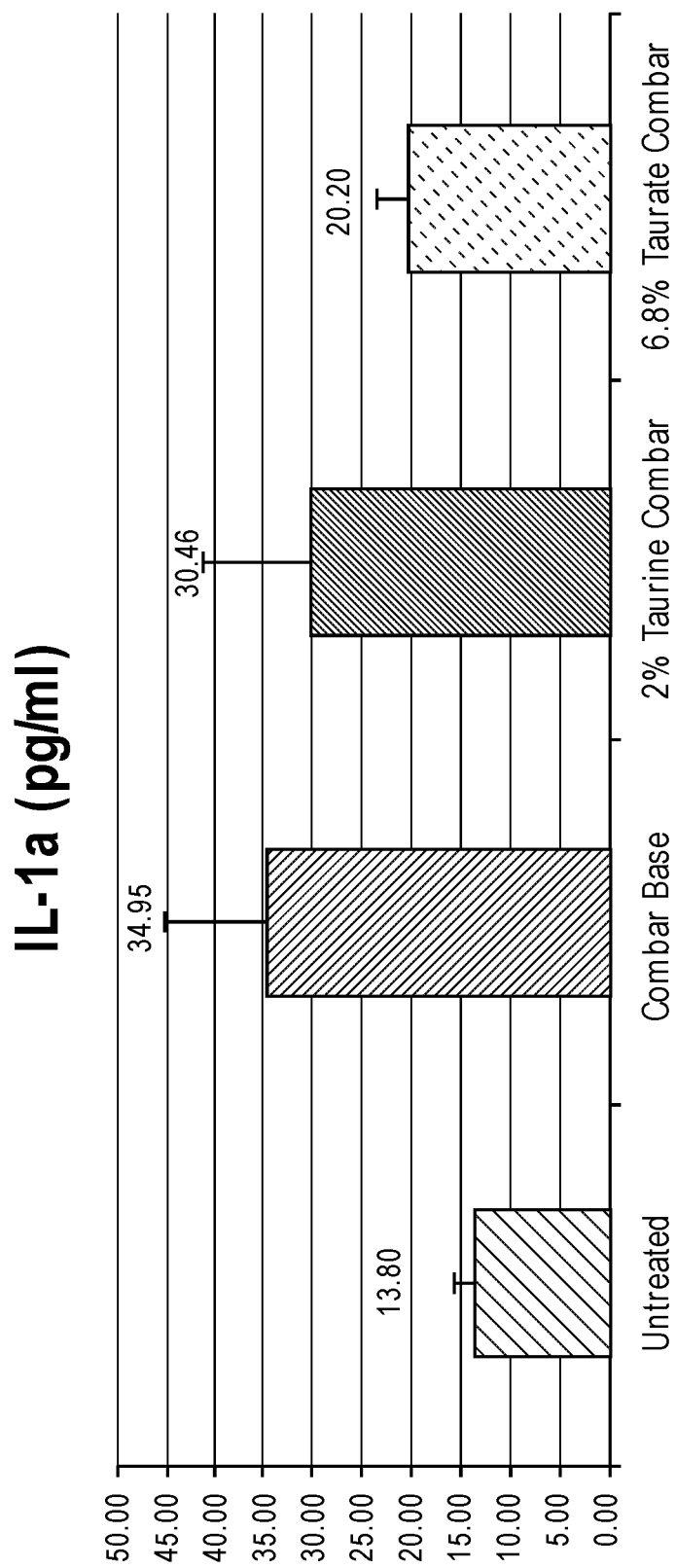
FIG. 3 shows IL-1a assay results from experiments performed using MatTek 3D EpiDerm and reported in pg/ml, as described in the Examples below.

As shown in FIG. 3, both the 2% taurine combar sample and the 6.8% sodium methyl oleoyl taurate combar sample (shown in graph as 6.8% taurate) had reduced IL-1a levels. Statistical analysis gave a p-value of 0.03 between the combar base and 6.8% sodium methyl oleoyl taurate combar and a p-value of 0.07 between the 2% taurine combar and the 6.8% sodium methyl oleoyl taurate combar. Thus, it can be concluded that sodium methyl oleoyl taurate significantly reduced the irritation potential of the combar base. The effect was comparable to taurine at the same molar concentration. These results suggest that sodium methyl oleoyl taurate can potentially be used in bar soap formulations as well as other product forms to deliver the skin benefits that have been previously documented with taurine.

What is claimed is:

1. A bar soap composition made from ingredients comprising:
    at least one cleanser chosen from soap; and
    at least one taurate surfactant chosen from a salt of a fatty acid amide of taurine, a salt of a fatty acid amide of N-methyl taurine, and combinations thereof,
    wherein the composition is in a solid bar form,
    wherein the bar soap composition does not include any surfactant other than the taurate surfactant and the soap, and
    wherein the at least one taurate surfactant is a compound of general formula 1:

$$R^1-\overset{O}{\underset{\|}{C}}-\overset{R^2}{\underset{|}{N}}-CH_2-CH_2-SO_3^- \ M^+ \quad (1)$$

wherein $R^1$ is a saturated or unsaturated, straight or branched alkyl or alkenyl group with 12 to 25 carbon atoms; $R^2$ is H or methyl and M is sodium, potassium, calcium, magnesium or ammonium.

2. The bar soap composition of claim 1, wherein the taurate surfactant is chosen from potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, sodium n-isostearoyl methyltaurate, calcium lauroyl taurate, magnesium methyl cocoyl taurate, sodium methyltaurate isopalmitamide, sodium methyltaurine cocoyl methyltaurate, sodium taurine cocoyl methyltaurate and mixtures thereof.

3. The bar soap composition of claim 1, wherein the taurate surfactant is sodium methyl oleyl taurate.

4. The bar soap composition of claim 1, wherein the bar soap composition does not include a medically effective amount of salicylic acid.

5. The bar soap composition of claim 1, wherein the taurate surfactant is present in an amount of 0.1% to 10% by weight of the composition.

6. The bar soap composition of claim 1, wherein the soap is a salt a $C_8$-$C_{22}$ carboxylic acid.

7. The bar soap composition of claim 1, wherein the soap has a pH of about 8.5 to about 12 in a 1 weight % aqueous solution.

8. A method of reducing skin irritation and/or inflammation, or of improving cellular repair function of the skin, comprising applying an effective amount of the composition of claim 1 to the skin of a subject.

* * * * *